United States Patent [19]

Long

[11] Patent Number: 5,309,903

[45] Date of Patent: * May 10, 1994

[54] METHOD FOR ADMINISTERING SURFACTANT TO THE LUNGS WHILE CONCURRENTLY PROVIDING ONE-LUNG VENTILATION

[75] Inventor: Walker A. Long, Chapel Hill, N.C.

[73] Assignee: Burroughs Wellcome Co., Research Triangle Park, N.C.

[*] Notice: The portion of the term of this patent subsequent to May 4, 2010 has been disclaimed.

[21] Appl. No.: 56,260

[22] Filed: Apr. 30, 1993

Related U.S. Application Data

[63] Continuation of Ser. No. 860,200, Mar. 26, 1992, Pat. No. 5,207,220, which is a continuation of Ser. No. 742,148, Aug. 1, 1991, abandoned, which is a continuation of Ser. No. 448,887, Dec. 12, 1989, abandoned.

[51] Int. Cl.$^5$ .................. A61M 15/00; A61M 16/10; A62B 9/06
[52] U.S. Cl. .................. 128/203.12; 128/207.14; 604/28; 604/49; 604/54; 604/56
[58] Field of Search .................. 128/200.24, 200.26, 128/203.12, 200.23, 207.14, 911, 912, DIG. 26; 604/28, 49, 54, 56, 93, 103, 94

[56] References Cited

U.S. PATENT DOCUMENTS

| | | | |
|---|---|---|---|
| 4,603,124 | 7/1986 | Takei et al. | 128/203.12 |
| 4,765,987 | 8/1988 | Bonte et al. | 128/203.12 |
| 4,826,821 | 5/1989 | Clements | 128/203.12 |
| 4,953,547 | 9/1990 | Poole, Jr. | 128/203.12 |
| 4,973,582 | 11/1990 | Yoshida et al. | 128/203.12 |
| 5,110,806 | 5/1992 | Clements | 128/203.12 |
| 5,207,220 | 5/1993 | Long | 128/207.14 |

OTHER PUBLICATIONS

M. Hallman et al., *Pediatrics 71*, No. 4, 473–482 (1983).
G. Enhorning et al., *Pediatrics 76*, No. 2, 145–153 (1985).
A. Wilkinson et al., *The Lancet Ltd.*, 287–291 (Aug. 10, 1985).
T. Des Jardins, in *Clinical Manifestations of Respiratory Disease*, (Year Book Medical Publishers, Inc.) pp. 312–326 (1984).
"Product Monograph. Synthetic Lung Surfactant for the Treatment of Neonatal Respiratory Distress." Publication by Burroughs Wellcome Co. (1990).

Primary Examiner—David A. Wiecking
Assistant Examiner—Kimberly L. Asher
Attorney, Agent, or Firm—Bell, Seltzer, Park & Gibson

[57] ABSTRACT

A method of administering a liquid pharmaceutical formulation, particularly a surfactant formulation, to at least one lung of a subject in need of such treatment is disclosed. The method is carried out while the subject has a breathing tube extending through the subject's mouth and larynx, and while ventilating at least one lung of the subject through the breathing tube. The method comprises simultaneously administering the liquid pharmaceutical formulation down the breathing tube and into at least one lung of the subject and ventilating at least one lung of the subject through the breathing tube. The method may be performed on premature infants to combat respiratory distress syndrome. A preferred apparatus for carrying out the method of the present invention comprises a breathing tube configured for insertion through a subject's mouth and larynx, a ventilating apparatus operatively associated with the breathing tube, and an injecting device such as a syringe operatively associated with the breathing tube for introducing a liquid pharmaceutical formulation into the breathing tube.

8 Claims, 1 Drawing Sheet

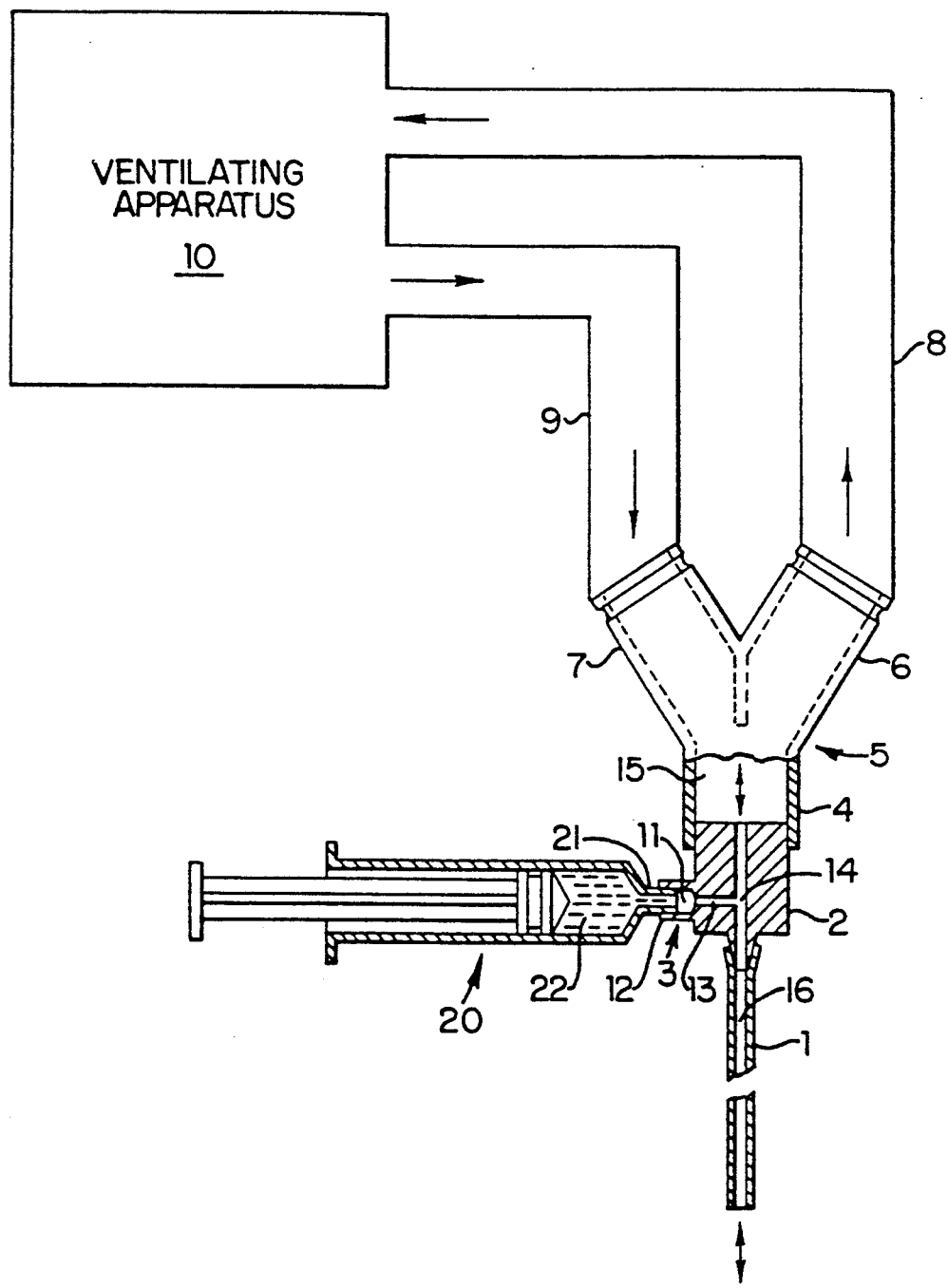

METHOD FOR ADMINISTERING SURFACTANT TO THE LUNGS WHILE CONCURRENTLY PROVIDING ONE-LUNG VENTILATION

This application is a continuation of Ser. No. 07/860,200, filed Mar. 26, 1992, issued as U.S. Pat. No. 5,207,220 on May 4, 1993, which is a continuation of patent application Ser. No. 07/742,148, filed Aug. 1, 1991, now abandoned, which is a continuation of patent application Ser. No. 07/448,887, filed Dec. 12, 1989, now abandoned.

FIELD OF THE INVENTION

The present invention concerns a method and apparatus for administering pharmaceutical formulations such as a surfactant formulation to the lungs of a subject in need of such treatment.

BACKGROUND OF THE INVENTION

Respiratory distress syndrome (RDS), also termed hyaline membrane disease, is the leading cause of death and disability among premature infants. Of the 230,000 to 250,000 infants born prematurely each year in the United States, 40,000 to 50,000 develop RDS; and of those who develop this disease, 5,000 to 8,000 die. The risk of RDS is less for infants born closer to full term. However, RDS occurs in up to 75% of infants born at less than 30 weeks of gestation (less than 1250 grams body weight). See generally R. Perelman and P. Farrell, *Pediatrics* 70, 570 (1982); D. Vidyasagar, in *Hyaline Membrane Disease: Pathogenesis and Pathophysiology*, 98 (L. Stern Ed. 1984).

RDS is caused by a deficiency in lung surfactant, a material ordinarily secreted onto the surface of lung alveoli. In the absence of surfactant, the alveoli tend to collapse during exhalation. Collapse can be avoided by mechanically ventilating the lungs. Nevertheless, even though premature infants often begin to secrete surfactant within 48 hours after birth, lung damage may have by this time already occurred due to the high oxygen concentrations and positive pressures of mechanical ventilation.

A number of groups have sought to develop surfactant formulations which can be used to treat or prevent RDS. Both human and bovine natural surfactants have been administered into the airways of newborn infants. See, e.g., J. Horbar et al., *N. Eng. J. Med.* 320, 959 (1989); R. Soll et al., *Pediatric Res.* 23, 425A (1988). Problems with such natural surfactants are, however, potential contamination with microorganisms and potential sensitization of the patient to proteins therein. Accordingly, completely synthetic surfactants have been developed. See. e.g. U.S. Pat. No. 4,826,821 to Clements; U.S. Pat. No. 4,312,860 to Clements.

With natural and synthetic surfactant formulations now available, a current problem is how to best administer them to a patient. Such patients are typically maintained on a ventilator with a breathing tube, an endotracheal tube extending through the patient's mouth and larynx. The endotracheal tube is joined to a ventilator Y-piece (typically through an endotracheal tube adapter), the Y-piece is connected to a pair of patient tubes, and the patient tubes are connected to a ventilating unit. The ventilating unit cyclically forces oxygen-rich air into, and allows oxygen-depleted air to escape from, the patient's lungs. One approach others have taken to administering a surfactant formulation to such a patient is to remove the Y-piece from the endotracheal tube adapter, inject the formulation into the endotracheal tube adapter, and rejoin the Y-piece to the endotracheal tube adapter. Another approach others have taken is to remove the Y-piece from the endotracheal tube adapter, insert a canula into the endotracheal tube adapter, inject the formulation through the canula, remove the canula, and rejoin the endotracheal tube adapter to the Y-piece. In both cases ventilation of the patient is interrupted. In both cases a risk of infecting the patient through the opened breathing tube exists. In both cases duration of administration is limited by the length of time which ventilation may be safely interrupted; and in both cases there is a need for substantial manipulation of the patient. These problems are compounded when the patient is a premature infant, particularly a premature infant afflicted with RDS, as such patients are sensitive to even gentle handling and susceptible to infection. Indeed, some premature infants critically ill with RDS do not tolerate even a brief interruption of mechanical ventilation.

Accordingly, an object of the present invention is to provide a method of administering a pharmaceutical formulation (particularly a surfactant formulation) to a patient's lungs without interrupting ventilation of that patient.

Another object of the present invention is to provide a method of administering a pharmaceutical formulation to a patient's lungs which does not require opening the breathing tube of that patient.

Another object of the present invention is to provide a method of administering a pharmaceutical formulation to a patient's lungs with a minimal number of manipulative steps to which that patient must be subjected.

SUMMARY OF THE INVENTION

A method of administering a liquid pharmaceutical formulation to at least one lung of a subject in need of such treatment is disclosed. The method is carried out while the subject has a breathing tube extending through the subject's mouth and larynx, and while ventilating at least one lung of the subject through the breathing tube. The method comprises simultaneously administering the liquid pharmaceutical formulation through the breathing tube and into at least one lung of the subject while ventilating at least one lung of the subject through the breathing tube. By simultaneous administration of the pharmaceutical formulation, the ventilation of the patient is carried on without interruption. In contrast, methods of administration carried out by others all require the interruption of ventilation.

In a preferred embodiment of the present invention, the method comprises: (a) providing a side port in the wall of the breathing tube; and (b) administering the liquid pharmaceutical formulation through the side port, down the breathing tube, and into at least one lung of the subject while simultaneously ventilating at least one lung of the subject through the breathing tube.

Also disclosed herein is an apparatus for administering a liquid pharmaceutical formulation to at least one lung of a subject in need of such treatment while simultaneously ventilating at least one lung of the subject. The apparatus comprises: (a) a breathing tube configured for insertion through a subject's mouth and larynx; (b) a ventilating apparatus operatively associated with the breathing tube; and (c) injecting means operatively associated with the breathing tube for introducing a liquid pharmaceutical formulation into the breathing tube.

BRIEF DESCRIPTION OF THE DRAWINGS

The Figure illustrates a preferred embodiment of the apparatus of the present invention. An endotracheal tube, endotracheal tube adapter, and syringe are shown in side sectional view, a ventilator Y-piece is shown with the distal arm broken away to illustrate the position of the endotracheal tube adapter therein, and a ventilating apparatus and pair of patient tubes are shown schematically. The direction of air flow in the apparatus is indicated by arrows.

DETAILED DESCRIPTION OF THE PREFERRED EMBODIMENTS

The terms "ventilate," "ventilation" and "ventilating" herein refer to the process of cyclically forcing oxygen-rich air into, and permitting oxygen-depleted air to escape from, at least one lung of a patient to assist the breathing of the patient or to breath for the patient when the patient would not otherwise breath on its own. Ventilation may be of either or both lungs of a patient, depending on whether any one lung is blocked, collapsed, or otherwise inoperable. For premature infants, the number of breaths set by the ventilating machine (one cycle of inhalation and exhalation) is from about 20 to about 60 breaths per minute (more commonly about 40 to about 60 breaths per minute in a sick baby).

The term "breathing tube," as used herein, refers to a single tube through which a patient is ventilated, which tube may be an integral tube or an assembly of adapters and tubes. The tube is configured so that, when inserted through a subject's larynx, the larynx is effectively sealed and air cannot effectively enter or escape from the subject's lungs without passing through the breathing tube. For example, a breathing tube may comprise, in sequence, the distal arm of a ventilator Y-piece, an endotracheal tube adapter, and an endotracheal tube. Endotracheal tubes are available in various sizes to provide the proper seal against the larynx in patients of different sizes. The term "breathing tube" excludes either of the pair of patient tubes connected to a ventilating apparatus, through one of which oxygen-rich air is forced to a patient and through the other of which oxygen-depleted air is withdrawn from a patient, and the two proximal arms of a ventilator Y-piece to which the ventilator patient tubes are joined. The volume of the breathing tube should be as small a quantity as possible to minimize dead space which can interfere with the patient's breathing.

While the present invention is primarily contemplated for use in administering surfactant formulations, any pharmaceutical formulation may be administered by the method and apparatus of the present invention. The lungs are rich in blood supply, hence certain pharmaceutical formulations may be administered into the lungs when other routes of administration are not available. For example, intravenous injection may be difficult to carry out in premature infants, necessitating administration to the lungs. Exemplary pharmaceutical formulations which may be administered to the lungs include, but are not limited to, formulations containing epinephrine, atropine, and acetylcholine. In pharmaceutical formulations the active ingredient is normally provided in a pharmaceutically acceptable carrier, such as sterile pyrogen-free water or physiological saline solution.

While a variety of pharmaceutical formulations may be administered by the method of the present invention, the present invention is intended primarily for use in treating human respiratory distress syndrome (RDS). The method may be carried out prophylactically (that is, on subjects at risk of developing RDS who have not yet developed RDS), or on subjects afflicted with RDS. While RDS occurs primarily in premature infants, it may also occur in infants, children, adolescents and adults as a result of disease or trauma. Hence, all such subjects may be treated by the method of the present invention. We have found the procedure to be well tolerated by premature infants.

Surfactant formulations used in practicing the present invention may be of any type useful for the treatment of RDS, whether of natural (i.e., human, bovine), see, e.g., J. Horbar et al., *N. Eng. J. Med.* 320, 959 (1989); R. Soll et al., *Pediatric Res.* 23, 425A (1988), recombinant, or synthetic origin, or combinations thereof. See,, e.g., Y. Tanaka et al., *J. Lipid Res.* 27, No. 2, 475 (1986), T. Fujiwara et al., *Lancet* 1, 55 (Jan. 12, 1980) (cow-lung extract fortified with dipalmitoylphosphatidylcholine). Particularly preferred for practicing the present invention is synthetic surfactant of the type described in U.S. Pat. No. 4,826,821 to Clements, the disclosure of which is to be incorporated herein by reference. Also useful for practicing the present invention is synthetic surfactant of the type described in U.S. Pat. No. 4,312,860 to Clements, the disclosure of which is to be incorporated herein by reference.

Because the method of the present invention does not require interruption of ventilation to administer the formulation, substantial volumes of a pharmaceutical formulation may be administered as one dosage unit simultaneously with (i.e., during) ventilation. Thus, at least about 1 cubic centimeter (cc) of formulation is preferably administered as one dose. In premature infants, a volume of formulation of between about 1 cc per kilogram (kg) body weight and about 8 cc/kg body weight is administered as one dose. The preferred volume administered in one treatment is 5 cc/kg in two separate doses of 2.5 cc/kg each.

In general, patients undergoing treatment by the method of the present invention are positioned so that the distal end of the breathing tube is lower than the side port in the breathing tube; as a result, administration of pharmaceutical formulation through the breathing tube is assisted by gravity. This positioning follows from the usual location of patient and equipment in most clinical settings.

Administration of the pharmaceutical formulation may be to either or both lungs of the patient, depending on whether any one lung is blocked or obstructed, and depending on the position of the patient with respect to gravity. It is desirable to vary the position of the patient to insure delivery of formulation to as many areas in the lungs as possible, and ideally to all five lobes of the lung. Four different positions (head down, right side up; head down, left side up; head up, right side up; head up, left side up) provide good distribution of the formulation within the lungs, but may be unnecessarily aggressive for infants critically ill with RDS who react to even gentle turning in bed with substantial decreases in arterial oxygen saturation. On the other hand, the beneficial effects of formulations such as surfactant formulations are likely to be greater when all lung areas are dosed.

Accordingly, turning the patient laterally 45 degrees to the right and 45 degrees to the left for various intervals during administration is preferably done to aid in uniform dosing.

In one preferred embodiment of the apparatus of the invention illustrated in the Figure, a subject (not shown) is intubated with an endotracheal tube 1, which extends through the subject's mouth and larynx. The endotracheal tube is connected to an endotracheal tube adapter 2 having a side port 3 formed therein. A suitable endotracheal tube adapter is shown in greater detail in U.S. Pat. Nos. 4,815,459 and 4,723,543, both to Beran, the disclosures of which are incorporated herein by reference. The endotracheal tube adapter shown in FIGS. 10-15 in the Beran patents is preferred for practicing the present invention. (Note specifically the female portion of Luer lock fitting 80, open-ended cavity 84, and passageway 40 in the embodiment shown in FIGS. 10-15 of Beran, which comprise side port 3 referred to herein.) This device is available from Respiratory Support Products, Inc., 3110 Alpine, Santa Anna, Calif., 92704; Telephone No. (714) 549-1265. The endotracheal tube adapter is connected to the distal arm 4 of a ventilator Y-piece (or "Y-tube") 5, either directly, as shown here and in the Beran patents, or indirectly through additional intervening tube(s) and/or adapters. Preferably, however, the volume of the breathing tube is kept to a minimum.

The two proximal arms 6, 7 of the ventilator Y-piece are connected to a pair of patient tubes 8, 9, and the pair of patient tubes are connected to a ventilating apparatus 10. Air flow in the component parts of this apparatus is indicated by arrows. Any ventilating apparatus may be employed, an example being the Servo-Ventilator 900 C/D ventilator manufactured by Siemens-Elma AB of Solona, Sweden.

A disposable syringe 20 is connected to the side port 3 of the endotracheal tube adapter, which syringe contains the pharmaceutical formulation to be administered the patient. Specifically, the nipple 21 of the syringe is inserted into the cavity 11 of the female portion of the Luer lock fitting 12 formed on the endotracheal tube adapter to provide a sealed engagement therewith, with the interior of the syringe containing the formulation 22 in fluid communication with the passageway 13 of the side port 3. The passageway 13 of the side port communicates with the Center bore 14 of the endotracheal tube adapter 2, with the center bore 14 of the endotracheal tube adapter interconnecting the interior 15 of Y-piece 5 and the center bore 16 of the endotracheal tube 1.

In use, the pharmaceutical formulation is injected into the endotracheal tube adapter center bore 14, where it flows down the endotracheal tube center bore 16 and into at least one lung of the patient. The pharmaceutical formulation is preferably injected slowly, so that it either flows down the side of the endotracheal tube into the patient or, if the formulation forms a plug in the tube, the plug is blown down the endotracheal tube into the patient.

While it is preferred to administer the pharmaceutical formulation by injection with a disposable syringe, as described above, any injecting means associated with the side port may be used which limits the escape of gas from the breathing tube during administration of the pharmaceutical formulation (e.g., pump, bulb, etc.).

More specific aspects of the present invention are explained in the following examples. These examples are provided for illustrative purposes only, and are not to be taken as limiting of the invention. In the examples, cc refers to cubic centimeters, mg refers to milligrams, and kg refers to kilograms.

EXAMPLE 1

Preparation of Surfactant Formulation 8 cc of sterile, pyrogen-free water is taken up in a sterile disposable syringe and injected into a sterile, evacuated, 10 cc vial containing a lyophilized powder of 108 mg dipalmitoylphosphatidylcholine (DPPC), 12 mg hexadecanol, 8 mg tyloxapol, and 46.75 mg NaCl. This mixture is known. See U.S. Pat. No. 4,826,821 to Clements. The water and powder are vigorously mixed by inverting the vial and repeatedly withdrawing the mixture into the syringe and releasing the plunger of the syringe. The result is 8 cc of surfactant formulation, which is a suspension rather than a solution. The formulation is 0.1N with respect to NaCl, has an osmolality of 190 mOsm/l, and contains 13.5 mg/cc of DPPC, 1.5 mg/cc of hexadecanol, and 1 mg/cc of tyloxapol.

EXAMPLE 2

Prophylactic Administration of Surfactant Formulation To a Premature Infant Subject The surfactant formulation prepared in Example 1 above is administered to a premature infant immediately after birth in a total amount of 5 cc/kg body weight.

The infant is placed on ventilation by insertion of an endotracheal tube through the infant's mouth and larynx. The endotracheal tube is connected to an endotracheal tube adapter having a right-angle Luer lock side port (available from Respiratory Support Products, Inc., 3110 Alpine, Santa Anna, Calif., 92704; Telephone No. (714) 549-1265). The adapter is connected to the distal arm of a ventilator Y-piece and the two proximal arms of the Y-piece are connected to a ventilating apparatus through a pair of patient tubes, as discussed above.

The 5 cc/kg total volume is administered in two separate 2.5 cc/kg doses. The first dose is administered with the infant laying on his or her back with the head in the midline position. Dosing in this position preferentially delivers surfactant formulation to the right lower lobe, and to the lingula and lower lobe of the left lung. Immediately after administration of the first dose, the infant is turned laterally 45 degrees to the right for 30 seconds. This maneuver is performed in order to facilitate delivery of the formulation to the right middle and right upper lobes. The infant is then turned back to the midline position. The second dose is then administered while the infant remains in the midline position. Immediately thereafter, the infant is turned laterally 45 degrees to the left for 30 seconds. This maneuver is performed in order to facilitate delivery of the formulation to the left upper lobe. Finally, the infant is returned to the midline position.

Each dose of formulation is injected in small boluses in synchrony with mechanical inspiration over 1 to 2 minutes (typically 30 to 50 mechanical breaths) as long as the infant tolerates the injection well. Injections are slowed or briefly halted if the infant reacts to the injection with agitation or changes in heart rate, color, transcutaneous arterial oxygen saturation, transcutaneous $PO_2$, or transcutaneous $CO_2$. The formulation is seen to flow down the side of the endotracheal tube into the subject, to form plugs in the tube which are blown into the subject, or to form plugs in the tube which are blown through by the ventilator, with the formulation then flowing down the side of the tube into the subject.

EXAMPLE 3

Administration of Surfactant Formulation to an Infant Subject afflicted with RDS The surfactant formulation prepared in Example 1 above is administered to a premature infant twenty-four hours after birth, which infant is afflicted with respiratory distress syndrome (RDS). The dose and manner of administration is the same as described in Example 2 above. A second dose is administered in the same manner twelve hours after the first dose to enhance the efficacy of the treatment.

The foregoing examples are illustrative of the present invention, and are not to be construed as limiting thereof. The invention is defined by the following claims, with equivalents of the claims to be included therein.

That which is claimed is:

1. A method of administering a liquid surfactant formulation to at least one lung of a subject in need of such treatment while ventilating at least one lung of the subject, the method comprising simultaneously administering the liquid surfactant formulation into at least one lung of the subject, and ventilating said at least one lung of the subject.

2. A method according to claim 1, wherein said ventilating step is carried out by cyclically forcing oxygen-rich air into, and permitting oxygen-depleted air to escape from, at least one lung of the subject.

3. A method according to claim 2, wherein said ventilating step is conducted at a rate of from about 20 to about 60 breaths per minute.

4. A method of administering a liquid stream of surfactant formulation to at least one lung of a subject in need of such treatment, the method comprising the steps of:

ventilating at least one lung of the subject with an oxygen-rich air stream;

providing introducing means for introducing a liquid surfactant formulation into said air stream; and administering the liquid surfactant formulation through the introducing means and into at least one lung of the subject while simultaneously ventilating at least one lung of the subject.

5. A method according to claim 4, further comprising the step of providing injecting means associated with the introducing means for limiting the escape of gas from the introducing means during administration of the surfactant formulation, and wherein the step of administering the surfactant formulation is carried out by injecting the surfactant formulation into the introducing means.

6. A method according to claim 4, further comprising the step of administering a volume of liquid surfactant solution of at least 1 cubic centimeter.

7. A method according to claim 4, wherein said ventilating step comprises cyclically forcing oxygen-rich air into, and permitting oxygen-depleted air to escape from, at least one lung of the subject.

8. A method according to claim 7, further comprising the step of conducting said ventilating step at a rate of from about 20 to about 60 breaths per minute.

* * * * *